United States Patent [19]

Boguslaski et al.

[11] Patent Number: 5,420,016
[45] Date of Patent: May 30, 1995

[54] TEST DEVICE AND KIT FOR DETECTING HELICOBACTER PYLORI

[75] Inventors: Robert C. Boguslaski; Robert J. Carrico, both of Elkhart, Ind.

[73] Assignee: Serim Research Corporation, Elkhart, Ind.

[21] Appl. No.: 198,236

[22] Filed: Feb. 18, 1994

Related U.S. Application Data

[63] Continuation-in-part of Ser. No. 856,992, Mar. 24, 1992, Pat. No. 5,314,804.

[51] Int. Cl.6 .................... C12Q 1/58; C12Q 1/04; G01N 21/00
[52] U.S. Cl. ........................ 435/12; 435/34; 436/169; 436/808; 422/58
[58] Field of Search ............ 422/56, 57, 58, 60, 422/61; 435/10, 12, 34, 805, 810; 436/169, 808, 810

[56] References Cited

U.S. PATENT DOCUMENTS

| | | | |
|---|---|---|---|
| 3,461,036 | 8/1969 | Harvill | 195/103.5 |
| 3,876,502 | 4/1975 | Monte et al. | 195/99 |
| 3,992,158 | 11/1976 | Przybylowica | 23/253 TP |
| 4,223,089 | 9/1980 | Rothe et al. | 435/12 |
| 4,548,906 | 10/1985 | Sekikawa et al. | 436/113 |
| 4,748,113 | 5/1988 | Marshall | 435/12 |
| 4,830,010 | 5/1989 | Marshall | 128/630 |
| 4,923,801 | 5/1990 | Marshall et al. | 435/12 |
| 5,139,934 | 8/1992 | Stewart | 435/7.92 |
| 5,314,804 | 5/1994 | Boguslaski et al. | 435/12 |

FOREIGN PATENT DOCUMENTS

| | | | |
|---|---|---|---|
| 0458231 | 11/1991 | European Pat. Off. | G01N 33/58 |
| 57-32557 | 6/1982 | Japan | H01J 37/28 |
| 57-66127 | 8/1982 | Japan | D01H 5/24 |

OTHER PUBLICATIONS

Butcher G., Use of an Ammonia Electrode . . . Digestion 1992 53 142–148.

Spayd, et al., Multilayer Film Element for Clinical Analysis: Applications to Representative Chemical Determinations, Clinical Chemistry, vol. 24, No. 8, 1343–1350 (1978).

*Primary Examiner*—William H. Beisner
*Assistant Examiner*—Ralph Gitomer
*Attorney, Agent, or Firm*—Baker & Daniels

[57] ABSTRACT

A rapid method and easy to use unitized test device is disclosed for determining the presence of *Helicobacter pylori* in a biological tissue specimen by detecting the presence of urease in the tissue. The system basically utilizes a multilayer test device for separating and optimizing the various reactions involved, i.e. the urease in the specimen with a substrate and the ammonia generated thereby with an indicator element.

15 Claims, 1 Drawing Sheet

TEST DEVICE AND KIT FOR DETECTING HELICOBACTER PYLORI

CROSS REFERENCE TO RELATED APPLICATIONS

This application is a continuation-in-part of application Ser. No. 856,992 filed on Mar. 24, 1992, now U.S. Pat. No. 5,314,804.

BACKGROUND OF THE INVENTION

1. Field of the Invention

The present invention relates to a rapid dry reagent chemistry test for *Helicobacter pylori*. More specifically, it relates to a test for determining the presence of a urease producing microorganism such as *Helicobacter pylori* in human gastric mucosa biopsy specimens.

2. Background Including a Description of the Related Art

In the diagnosis and management of gastrointestinal disorders, the determination of *Helicobacter pylori* (formerly known as *Campylobacter*) is becoming increasingly important. The presence of spiral or curved microorganisms in biopsy specimens of human gastric mucosa has been recognized for several decades [Freedberg, A. S. and Barron, L. E., The presence of spirochetes in human gastric mucosa, AM. J. Dis. Dis., 7: 443–5, (1940)]. A bacterium with curved morphology was cultured from gastric-biopsy specimens from patients with gastritis in 1982 [Warren, J. R., Unidentified curved bacilli on gastric epithelium in active chronic gastritis, Lancet, 1:1273, (1983)] and has recently been named *Helicobacter pylori*. Clinical research since 1982 indicates that *H. pylori* has a role in causing some forms of gastritis and might also be involved in the pathogenesis of peptic ulcers [Peterson, W. L., *Helicobacter pylori* and peptic ulcer disease, New Eng. J. Med., 324: 1042–8, (1991)].

*H. pylori* grows on the gastric epithelium and does not penetrate the tissues. It is also fecund on tissue from the esophagus and duodenum. The bacterium appears to be protected from stomach acid by the action of a urease which the bacterium produces. The urease has very high specific activity [Dunn, B. E., et al., Purification and characterization of urease from *Helicobacter pylori*, J. Biol. Chem., 265: 9464–9, (1990)] and hydrolyzes endogenous urea from the host tissues to form ammonia which neutralizes stomach acid.

A recent publication suggests that the best means to diagnose *H. pylori* infections in gastric mucosa biopsies is a combination of culture and direct microscopic observation of the microorganism on tissue following histologic staining (Peterson, W. L., op. cit.). However, the value of culture for this purpose has been questioned [Martinez, E. and Marcos, A., *Helicobacter pylori* and peptic ulcer disease, Lancet, 325: 737, (1991)].

An alternative test for *H. pylori* utilizes its urease activity. A mucosal biopsy specimen is incubated in a medium containing urea and a pH sensitive dye [Owen, R. J., et al., Rapid urea hydrolysis by gastric *Campylobacters*, Lancet, 1: 111, (1985)]. Urease produced by *H. pylori* releases ammonia through hydrolysis of urea and when enough ammonia is produced to raise the pH of the medium the dye changes color. Human tissues do not produce urease and *H. pylori* is the principal urease producing microorganism that inhabits the stomach. Occasionally biopsy specimens contain other urease producing bacteria that grow in the assay medium during the incubation and produce a false positive result [Marshall, B. J., et al., Rapid urease tests in the management of *Campylobacter pylori*]. The urease test for *H. pylori* relies on preformed urease and cell growth is not required; therefore, the specificity of the test is improved by including a bactericide in the medium. This inhibits the growth of other microorganisms that might contaminate the specimen (loc. cit.).

A commercial test for *H. pylori*, named CLOtest, described and claimed in U.S. Pat. No. 4,748,113, detects urease activity on biopsy specimens. The incubation medium is solidified by including a gelling agent. This medium also contains phenol red which turns pink when ammonia released from urea raises the pH above 6.0. The system is buffered so that specimens contaminated by fluids from the intestine do not raise the pH and cause a false positive result. When specimens are first inserted into the CLOtest gel they may have a slight pink tinge if blood or alkaline bile is present. The analyst is required to record the initial appearance of the specimen. The test is positive only if the pink color increases in intensity or area.

CLOtest requires three hours incubation at 30° C. and up to 21 hours additional incubation at room temperature. About 75% of biopsy specimens infected with *H. pylori* give positive results in 20 minutes and 90% are positive by 3 hours. Twenty-four hours are required to verify negative results because 5% of infected specimens become positive between 3 and 24 hours.

The traditional liquid urease tests use a few hundred microliters of medium and ammonia produced by a positive specimen becomes mixed with the medium by diffusion and mechanical stirring. The CLOtest reduces mechanical stirring by using gelled medium and specimens with high urease activity will produce a red color near the specimen in a short time. However, ammonia produced slowly by weakly positive specimens has time to diffuse throughout the gel and a larger amount of ammonia must be produced to give a color change. Thus, the incubation time required for a color change increases disproportionately as the urease content of the specimen decreases. In addition the buffer included in the test medium to consume acid or base on the specimen inhibits pH changes due to production of ammonia and this reduces assay sensitivity and increases incubation times.

SUMMARY OF THE INVENTION

The present invention involves a method, device and kit for determining the presence of *Helicobacter pylori* in a biological specimen by detecting the presence of urease using a system for separating and optimizing the various reactions involved. The biopsy specimen is first reacted with a urease substrate under optimized pH conditions on one side of a diffusion membrane element. The ammonia generated by the reaction of urease with the substrate, i.e. urea, permeates to the other side of such membrane where it comes into contact with an optimized indicator element to produce a detectable response.

DESCRIPTION OF THE PREFERRED EMBODIMENTS

The present invention is characterized by isolation of an optimized specimen and substrate reaction to produce ammonia from an optimized test indicator reaction to detect the generated ammonia. By doing this, the sample components do not interfere with the indicator and the sample can be incubated at a pH that is optimal for urease. Also, buffer in contact with the specimen does not have an adverse effect on assay sensitivity. This separation mechanism can be illustrated by the following detailed descriptions of the drawings.

Figure 1:
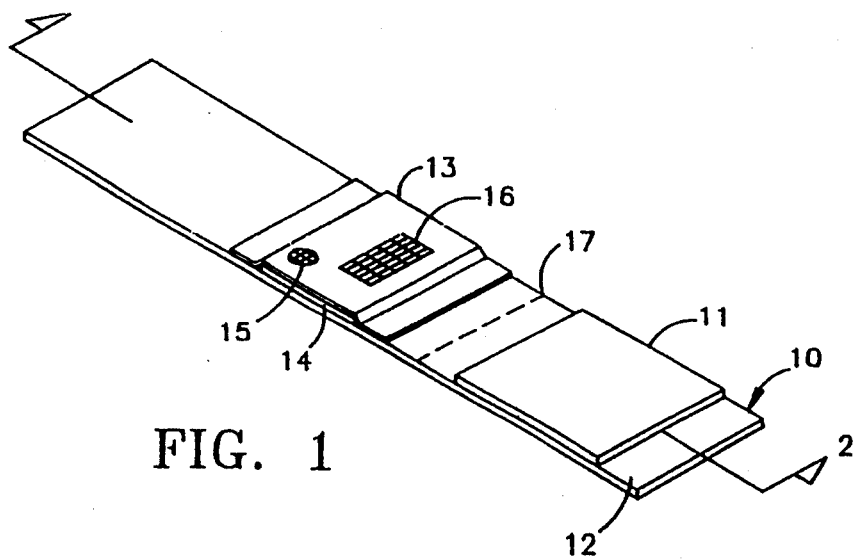
FIG. 1 is a perspective view of a unitized test device showing the placement of the various layers before use.

FIG. 1 is a perspective view of a device of the present invention. A strip like test device 10 is made up of a substrate element 11 consisting of an absorbent paper matrix containing the buffered dried residue of a substrate for urease, i.e. urea which paper matrix is attached to a clear plastic support member 12 using double faced adhesive tape. An indicator element 14 consisting of an absorbent matrix containing the dried residue of a pH sensitive indicator material, the indicator element 14 being covered with a diffusion membrane element 13, is attached to the support member 12 at the edges of the indicator element 14. The substrate element 11 and the indicator element 14 are positioned on the support member 12 such that when the device is folded at perforation line 17, the two elements are contiguous to or become adjacent to one another. FIG. 1 also shows a grid 16 for positioning the sample and a control 15 comprising urease attached to the diffusion element 13.

Figure 2:
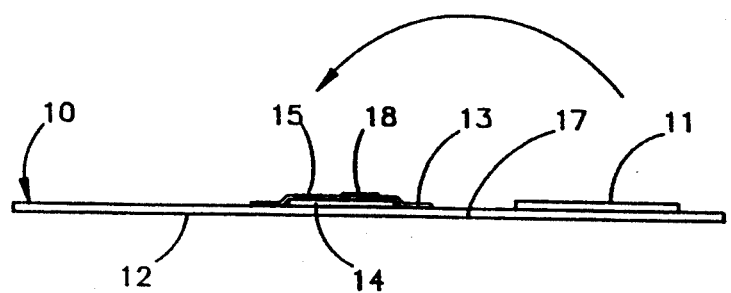
FIG. 2 is a longitudinal sectional view of the device of FIG. 1 shown with the specimen added. The curved arrow shows how the device is folded over on itself in use.

FIG. 2 is a sectional view of device 10 of FIG. 1 taken along the lines 2—2. A specimen 18 is shown positioned on the surface of the diffusion element 13. The arrow above the device shows how the device is folded over on itself.

Figure 3:
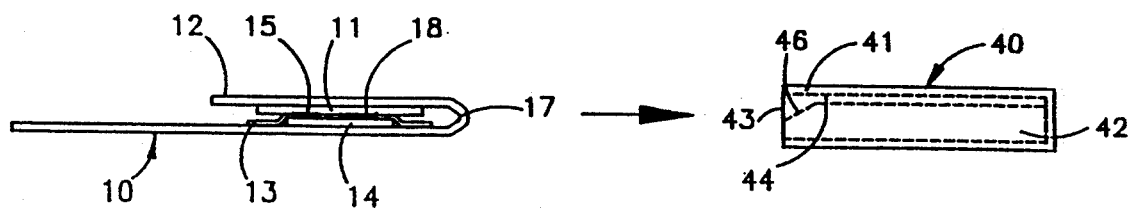
FIG. 3 is the same sectional view as in FIG. 2 except that the device has been folded on itself and is ready for insertion into a holder therefor.

FIG. 3 shows the device of FIG. 1 when it is folded over on itself. A control 15 and a specimen 18 are positioned between the substrate element 11 and the diffusion element 13. FIG. 3 further shows a holder 40 for the folded device 10 which holder consists of a clear plastic open ended box 41 having several raised ribs 42 with a sloping front edge 46, which ribs 42 extend from the bottom upward allowing a space between their upper edges 45 and the top of the box 44 to allow insertion of the folded device 10 therein, the distance between the upper edges 45 and the top 44 sufficient for acceptance of the device 10 in a folded position and retention of the various elements and test samples in intimate contact during reaction thereof.

Figure 4:
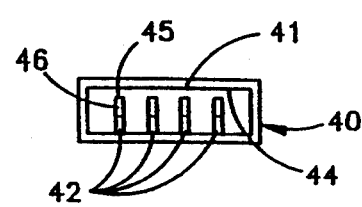
FIG. 4 is a front end view of the holder shown in FIG. 3.

FIG. 4 shows the front open end of holder 40 with four device support ribs 42 being shown equally spaced inside the box.

Figure 5:
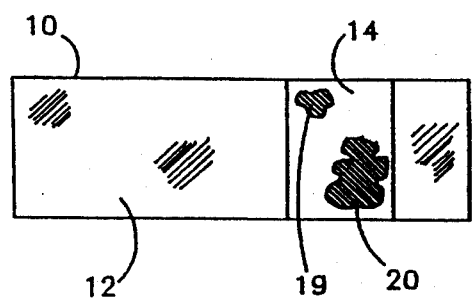
FIG. 5 is the reverse side of the device showing a positive result for the control and specimen.

FIG. 5 shows the reverse side of the device 10 of FIG. 1 after reaction has taken place to give a positive response to urease in the indicator element 14, which is read through the clear support element 12 to indicate a positive result for the control 19 and the specimen 20.

The methods and devices of the present invention utilize several components which are fabricated as a multilayered multielement test device. The several components basically comprise 1. a substrate element to contain the urease substrate under optimized reaction conditions, 2. a diffusion element to separate the various reactions and allow ammonia to pass and 3. an indicator element to give an indicia or response to a positive result. Each of these components and the assembly thereof will be described below.

Diffusion Element

Diffusion elements (membranes) must be hydrophobic to prevent passage of liquid water and solutes. Diffusion of water vapor through this membrane is acceptable because this will not neutralize the indicator dye.

Diffusion membranes should be as thin as possible in order to minimize the length of the diffusion path for ammonia. The practical lower limit for membrane thickness is determined by the quantity of material required to maintain mechanical integrity of the membrane. Commercial membranes range from 50 to 250 microns thick.

Mean pore diameters for commercial membranes range from 0.05 to 10 microns. Membranes with the larger pore diameters offer less resistance to diffusion of ammonia. Thus, pore diameters of 1.0 to 10 microns are preferable for present applications.

Hydrophobic membranes can be cast with a variety of polymers. They include polyvinylidene difluoride, polytrifluoroethylene, polyvinyl chloride, polypropylene, polyvinylidene dichloride and polytetrafluoroethylene.

Indicator Element

Indicator elements can be either hydrophilic or hydrophobic. They serve mainly as a support or matrix for the indicator dye and should have a large surface area to maximize exposure of the dye to ammonia gas diffusing through the diffusion membrane. The indicator element will be viewed from the side opposite the diffusion membrane, therefore, it is advantageous for the indicator element to be thin so color changes on the diffusion membrane side will be more readily visible to an observer. Microporous membranes are useful diffusion elements because they are thin. Large pore diameters favor rapid diffusion of ammonia to the dye coating. Woven or non-woven fabrics can also be used for the indicator element but they are generally thicker than microporous membranes.

The hydrophobic membranes mentioned above for diffusion membranes can be used as indicator elements. Hydrophilic membranes are also useful and they can be fabricated from cellulose esters, nitrocellulose, nylon, polysulfone and hydroxylated polyvinylidene difluoride.

Indicator elements will generally be coated or impregnated with indicator by dipping them into a solution of the indicator and drying. The amount of indicator applied can be varied by varying the indicator concentration in the dip solution.

Substrate Element

One purpose of the substrate element is to expose the biopsy specimen to urea. A second function is to adjust the pH of the specimen to the optimum for urease activity and for formation of ammonia through the ammonia/ammonium ion equilibrium. Thus, the substrate element will contain a buffer, urea and possibly reagents that enhance the activity of urease such as EDTA.

The substrate element matrix can be cellulose based papers, the hydrophilic membranes mentioned above or a woven or nonwoven fabric. Reagents will be incorporated by dipping the matrix into an aqueous solution of the reagents and drying.

Biopsy specimens might not contain enough water to dissolve the dry reagents in the substrate element and give maximum enzyme activity. In this situation, the substrate element can be hydrated by applying a few drops of water. Biopsy specimens are placed on the diffusion membrane and a wet substrate element is placed on them. The assembly is held together with a clamp.

Alternatively, a substrate element can be prepared by dipping the matrix in a urea solution and drying. When the test is to be initiated the substrate element is hydrated with a buffer solution which will maintain the proper pH and other reaction conditions.

Devices can also be assembled with a thin membrane as substrate element mounted on the diffusion membrane. Then biopsy specimens are placed on the substrate element and they are covered with a paper wick that does not contain reagents but is saturated with water. In this situation the substrate element should be a thin porous membrane because ammonia must diffuse through it to reach the indicator element.

The substrate element contains a buffer at pH 7.0 to 9.0. The pH optimum for *H. pylori* urease is 8.2 [Mobley, et al., J. Clin. Microbiol., 26:831-6 (1988)]. The pKa for ammonium ion is 9.3 and higher pH favors formation of ammonia from ammonium ion. A pH between 8.0 and 8.5 would be optimal for maximum urease activity and ammonia diffusion.

Urease from *H. pylori* has a Michaelis constant of 0.3 mM urea [Dunn, et al., J. Biol. Chem., 265:9464-9 (1990)]. Thus, urea concentrations of 5 mM or higher in the substrate element should provide nearly maximum enzyme activity.

Positive Control

A positive control can be included in a test device by introducing a small amount of urease onto the device at a location away from the specimens being tested. Ureases from various sources have properties similar to *H. pylori* urease; therefore, jack bean urease for instance can be used to make a positive control. The enzyme can be impregnated into a matrix such as cotton string and dried. The string can be mounted at the desired location on the diffusion membrane and when the wet substrate element is placed on the diffusion membrane the positive control urease will become active and generate ammonia. The time required to give a visible response with the positive control can be adjusted by adjusting the amount of urease incorporated into the string. An alternative method for including the positive control into the test device would be to incorporate the urease into a suitable composition and simply applying the composition to the diffusion element and drying.

pH Indicators

An ideal pH indicator for inclusion in the indicator element would change from a colorless to a colored form when a proton is removed by ammonia. However, most indicators change from one color in the acid form to another color in the deprotonated form. To obtain reasonable sensitivity with the present test the indicator should change from a weak color such as yellow in the protonated form to a strong color such as red or blue in the basic form.

An additional function of indicator dyes is to trap ammonia as ammonium ion and this is achieved more efficiently when the pKa of the dye is low compared to that for ammonium ion, pKa=9.3.

| Indicator | pKa |
|---|---|
| Cresol Red | 8.3 |
| Phenol Red | 7.9 |
| Bromocresol Purple | 6.3 |
| Chlorophenol Red | 6.0 |
| Bromocresol Green | 4.5 |
| Bromophenol Blue | 4.0 |

Cresol red and phenol red dried in membranes are not acidic enough to give a color change in the presence of low levels of ammonia. Bromocresol purple and chlorophenol red give satisfactory responses to ammonia if they are dried into a membrane with about 40% glycerol. The glycerol acts as a humectant and/or solvent. Bromophenol blue responds to ammonia without glycerol present and the color remains stable for at least a few hours if the test device is not opened to the atmosphere. Preferably the pKa of the indicator dye should be less than 8.0 and still more preferably should be within a range of about from 2.0 to 6.0.

Assembly of Devices and Method of Use

The devices and test kits of the present invention can be assembled and used in several ways. One advantageous way to assemble devices has been described above and shown in the drawings. Basically, the diffusion element is positioned between the substrate element and the indicator element. However, it must be appreciated that the urease in the specimen must be reacted with the substrate to generate ammonia and the ammonia must reach the indicator element. One utilitarian method to achieve this result is to place the specimen on the diffusion element which is held in contiguous relationship with the indicator element and bring the substrate into contact with the side of the diffusion element opposite the indicator element. This can be achieved most conveniently by positioning both the substrate element and diffusion element (contiguous with the indicator element) on a clear plastic foil support in an end to end or side by side relationship such that the specimen can be added directly to the diffusion element, rehydrating fluid added to the substrate element and the device folded over on itself to form a multilayered multielement device where the specimen is sandwiched between the substrate element and the diffusion element. Moreover, means, such as a clamp or holder which exerts an even overall pressure on the folded device (and the components thereof), may be utilized to keep the substrate element and the diffusion element in intimate contact with the tissue specimen included therebetween which allows the reaction of the various components with the tissue specimen to proceed in an expeditious manner.

Under certain circumstances it may be necessary to adjust the sensitivity of the test devices of the present invention. For example, there may be ammonia or other ammonia producing substances in or accompanying the fluids associated with the tissue specimens undergoing testing for urease. Such sensitivity adjustments may be accomplished by adding to the diffusion element and/or indicator element, predetermined amounts of chemicals or adsorbants which react quickly with or tie up the initial surge of ammonia through the diffusion element. By doing this, only the ammonia generated by the urease in the tissue specimen will react with the indicator in the indicator element to give a positive response.

A particularly useful embodiment of the present invention involves assembling the various system components into a test kit which makes its use more convenient and facile for the test operator. Such a test kit advantageously would comprise the test device shown in FIGS. 1-5 as well as a rehydrating solution for the substrate pad and a holder as shown in FIGS. 3 and 4 for retaining the test device in a folded position during the reaction of the urease in the test specimen with the various test reagent components. The rehydrating solution may simply be purified water or a buffer solution for optimizing the reaction of the urease in the test sample with the urea in the substrate element. Placement of the buffer in the rehydrating solution obviates the need for including the buffer in the substrate element along with the urea. Alternatively, the various components of the test system may be constructed as separate items and the individual components assembled at the time of use. For example, the substrate element, the diffusion element and the indicator element may be separate components which upon use are assembled into a test device as described herein as opposed to unitizing the various components as shown in FIG. 1. Moreover, the rehydrating solution may be simply water or may be an aqueous buffer solution having a pH of from about 7.0 to 9.0. However, when water is used as the rehydrating fluid, the buffer should be included as a component of the substrate element.

The following examples are illustrative of the present invention.

EXAMPLE 1

Preparation of Synthetic Biopsy Specimen

Jackbean urease (from GDS Technology, Inc., Elkhart, Ind.) was dissolved at 2.0 mg/mL in 0.02M potassium phosphate buffer, pH 7.3, 1 mM ethylenediaminatetracetic acid (EDTA). Dilutions of this stock enzyme solution were assayed for activity as follows:

The assay was conducted at 30° C. in 0.15M sodium phosphate buffer, pH 7.7. One milliliter reactions contained 1.0 mM ADP, 0.25 mM NADH, 1.0 mM --ketoglutarate and 15 units/mL glutamic dehydrogenase (bovine liver, Sigma, St. Louis, Mo.). The mixture was incubated at 30° C. for about four minutes until the absorbance at 340 nm stabilized. Then urease was added and the change in absorbance from 200 to 260 seconds later was recorded. One unit of urease activity hydrolyzes one micromole of urea per minute.

Cotton wound polyester thread was submerged in a solution containing 0.43, 1.33 and 3.83 units of urease/mL for five minutes. Then the threads were removed and dried in an oven at 60° C. for five minutes.

Substrate Element

Rayon fabric, grade No. 9343732 manufactured by Veratec, Inc., Walpole, Mass., was dipped into a solution containing 100 mM sodium phosphate buffer, pH 8.0, 1.0 mM EDTA and 100 mM urea. Then the fabric was dried at 60° C. for 10 minutes.

Diffusion Element

Hydrophobic Versapel 10000 membrane obtained from Gelman Sciences, Ann Arbor, Mich. was employed.

Indicator Element

A solution of reagent alcohol-water (1:9) containing 1.5 mg bromophenol blue/mL (water soluble form, Aldrich Chemical Co., Milwaukee, Wis.) and 15 mM sulfamic acid was impregnated into Versapor 10000 membrane available from Gelman Sciences and then the membrane was dried at 60° C. for seven minutes. (Reagent alcohol was 90% ethanol, 5% methanol and 5% isopropanol.)

A solution of ethanol-water (1:9) containing 1.5 mg bromophenol blue/mL and 2.0 mM sulfamic acid was impregnated into hydrophilic Durapore membrane (Millipore Corp., Bedford, Mass.). Then the membrane was dried at 60° C. for five minutes.

Tests with Urease Impregnated Threads

Test devices were assembled by placing a 1.0×1.0 cm square of Versapor indicator membrane on a 2×5 cm piece of PP2500 transparency film (3M Corp., Minneapolis, Minn.). The indicator membrane was covered with 1.5×1.5 cm square of Versapel 1000 membrane (diffusion membrane). The membrane stack was fastened in place with overlaminating tape with a 6 mm diameter hole cut to provide access to the diffusion membrane. A 5 mm segment of thread impregnated with urease was placed on the diffusion membrane and covered with a 1.0×1.0 cm piece of substrate element that was saturated with water. This element was fastened in place with tape.

Threads impregnated with solutions containing various levels of urease were tested in devices. The indicator element was yellow due to the protonated form of the indicator dye and positive results with urease impregnated threads appeared as blue areas roughly outlining the shape of the underlying thread. The time required to obtain positive results with threads impregnated with different levels of urease are presented below along with the times that identical pieces of thread gave to positive results in CLOtest.

| Urease in Impregnating Solution (units/mL) | Time for Positive Result | |
|---|---|---|
| | Diffusion Device | CLOtest |
| 0 | No pos. result | No pos. result |
| 0.43 | 60 min | No pos. result |
| 1.3 | 20 min | 24 hrs |
| 3.8 | 11 min | 1.5 hrs |

It is apparent that the diffusion device gives positive results much more quickly than the CLOtest.

EXAMPLE 2

Another diffusion device was made with the hydrophilic Durapore membrane (Millipore Corp., Bedford, Mass.) impregnated with bromophenol blue as indicator element. Thread impregnated with 3.8 units urease/mL gave a positive result in seven minutes.

EXAMPLE 3

A test device for detecting *Helicobacter pylori* by assaying for urease activity was prepared as follows:

Substrate Element

Filter paper #237 manufactured by Ahlstrom Filtration, Inc., Mt. Holly, Pa. was dipped in a solution composed of 250 mM sodium phosphate, pH 8.0, 250 mM urea and 1.0 mM EDTA. Then the paper was dried at 60° C. for 10 min.

Diffusion Element

Versapel 10000 membrane.

Indicator Element

Bromophenol blue (sultone form—Aldrich Chemical) was dissolved at 2.0 mg/mL in reagent alcohol. Versapel 10000 membrane was dipped in this solution and then dried at 60° C. for 5 min.

Assembly of Devices

A 2×2 cm piece of Scotch double coated polyester film tape #90729 (3M Corp.) was attached to a piece of PP2500 transparency film and a 1×1 cm square of indicator membrane was fastened at the center of the tape. A 2×2 cm piece of untreated Versapel 10000 diffusion membrane was placed over the indicator membrane so the outer edges of the diffusion membrane were held in place by the tape. A 2×2 cm piece of substrate element was fastened to transparency film with Scotch double coated polyester film tape.

Test with Urease Containing Matrix

A 5 mm segment of urease impregnated thread was placed on the diffusion membrane over the yellow indicator membrane. A few drops of water were applied to the substrate element and it was placed on top of the thread on the diffusion membrane. The assembly was held together with a clamp and the indicator membrane was observed for a color change. Blue areas outlining the shape of the urease impregnated threads become visible at the following times:

| Urease in Impregnating Solutions (units/mL) | Time of Appearance of Blue Color (min) |
|---|---|
| 0.43 | 50 |
| 1.3 | 11 |

EXAMPLE 4

This example represents the use of a device of the present invention to determine *Helicobacter pylori* in an actual biopsy specimen.

Assembly of Devices

A 1×1.25 inch piece of substrate element as prepared in Example 3 above was fastened with polyester film tape to one end of a 1×4.8 inch piece of 0.01 inch thick clear polystyrene film. An indicator element was made by impregnating Versapel 5000 membrane with bromphenol blue as described in Example 3 next above. A 0.75×1 cm piece of indicator element was placed 0.75 inch from the substrate element on the polystyrene film. The indicator element was covered with a 1×1.25 inch piece of Versapel 5000 membrane (diffusion element) and the overlapping edges fastened to the polystyrene film with strips of polyester film tape.

The following materials were mixed in a mortar and pestle to obtain a viscous solution:

| 1.4 g | Polyvinyl Alcohol (2000 MW, 75% hydrolyzed) |
|---|---|
| 2.4 ml | 0.02 M Potassium Phosphate Buffer, pH 7.2, 1.0 mM EDTA |
| 0.4 ml | 4 mg Congo Red/ml water |
| 0.026 ml | 385 Units Urease/ml buffer |

One end of a 2 mm diameter stainless steel rod was dipped into the viscous solution and touched against the diffusion element near one corner. This provided a positive control spot and was allowed to dry.

Test with Biopsy Specimens

Three biopsy specimens were taken from the stomach of a patient suffering from a gastric disorder and were placed about 3 mm apart on the diffusion element of the test device. The substrate element was rehydrated with five drops of water containing 1 mg of sodium azide per ml. The device was folded on itself as described herein such that the substrate element came into contact with the specimen and the diffusion element and device was fastened with a clamp to ensure continued contact.

Within three minutes blue spots appeared on the opposite side of the polystyrene support where the specimen was placed indicating that urease was present. By 6 to 7 minutes a blue spot appeared in the area adjacent to the positive control.

EXAMPLE 5

Substrate Element

Ahlstrom 237 paper was dipped into 10 mM urea in water and dried at 60° C. for 1 to 15 minutes.

Indicator Element

A 100 mM sulfamic acid solution was prepared by dissolving 242 mg of the acid in 5 ml of water and then adding 20 ml reagent alcohol. Two dip solutions were prepared. The first used 2.5 ml of the sulfamic acid solution, 2.5 ml reagent alcohol and 10 mg bromphenol blue. The second used 1.25 ml of the sulfamic acid solution, 3.75 ml reagent alcohol and 10 mg bromphenol blue. Versapel 5000 membranes were impregnated with these solutions and dried at 60° C. for 5 minutes.

Construction of Devices

The indicator membranes described above were made with dips containing 25 and 50 mM sulfamic acid. Test devices were constructed with each of these membranes as described in Example 4. The substrate paper described in the present Example and Versapel 5000 membrane were the substrate and diffusion elements, respectively.

Tests with Urease Impregnated Thread

Segments of thread, 5 mm, impregnated with 1.33 units urease/ml (Example 1) were placed on the diffusion membranes of test devices. Then the substrate element was hydrated with 100 mM TRISHCl, pH 8.2, 1.0 mM EDTA. 0.1% sodium azide. The substrate elements were folded over onto the diffusion membranes and clamped in place. The times required for distinct blue images of the threads to appear were recorded. The indicator element made with dip containing 25 mM sulfamic acid required 25 to 35 minutes for the image to appear and the one made with dip containing 50 mM sulfamic acid required 55 to 65 minutes.

What is claimed is:

1. A multilayer test device for detecting urease in biological tissue specimens comprising:
   A. a substrate element comprising a matrix containing a substrate for urease;
   B. a diffusion element comprising a membrane permeable to ammonia and impermeable to water;
   C. an indicator element comprising a matrix containing a means for detecting ammonia, the indicator element being in contiguous relationship with the diffusion element;
   D. wherein a predetermined quantity of sulfamic acid sufficient to react with ammonia to produce a desired sensitivity is present in the indicator element or the diffusion element; and
   E. means for placing and maintaining a biological tissue specimen between the substrate element and the diffusion element.

2. The device of claim 1 wherein the substrate element contains urea.

3. The device of claim 2 wherein the substrate element matrix is absorbent paper.

4. The device of claim 1 wherein the substrate element includes a buffer to maintain the pH of the matrix in a pH range of from about 7.0 to 9.0.

5. The device of claim 1 wherein the means for placing and maintaining a biological tissue specimen between the substrate element matrix and the diffusion element is a support member comprising a clear plastic foil on which the substrate element matrix and the diffusion element are placed in a side by side relationship such that when a biological tissue specimen is placed on the diffusion element, the substrate element may be folded over including the specimen therebetween.

6. The device of claim 1 wherein the means for detecting ammonia is a pH sensitive dye having a pKa of about from 2.0 to 8.0.

7. The device of claim 1 wherein the diffusion element is a membrane having a pore size of about from 0.05 to 10 microns.

8. The device of claim 1 wherein a predetermined amount of urease is placed on the diffusion element and acts as a positive control for the test device.

9. A test kit for detecting urease in biological tissue specimens comprising:
   A. an aqueous rehydrating solution;
   B. a buffer having a pH of about from 7.0 to 9.0;
   C. a substrate element comprising a matrix having therein a dried residue of urea;
   D. a diffusion element comprising a membrane permeable to ammonia and impermeable to water;
   E. an indicator element comprising a matrix containing a dried residue of a pH indicator having a pKa of about from 2.0 to 6.0 for detecting ammonia, the indicator element being in contiguous relationship with the diffusion element;
   F. wherein a predetermined quantity of sulfamic acid sufficient to react with ammonia to produce a desired sensitivity is present in the indicator element or the diffusion element; and
   G. means for placing and maintaining a biological specimen between the substrate element and the diffusion element whereby any urease in the biological specimen will react with the urea to generate ammonia which will permeate the diffusion membrane and be detected by the indicator element.

10. A test kit as in claim 9 wherein the substrate element matrix and the indicator element are attached to a common support member in a side by side relationship allowing one to be folded over onto the other.

11. A test kit as in claim 10 wherein the kit contains a holder or clamp for the common support member to be retained in a folded position.

12. A test kit as in claim 9 wherein urease is positioned on the diffusion element apart from the biological specimen position which urease acts as a positive control for the test kit.

13. A test kit as in claim 9 wherein the aqueous rehydrating solution and the buffer are combined to form a common solution.

14. A test kit as in claim 9 wherein the buffer is contained in the substrate element.

15. A test kit as in claim 9 wherein a predetermined amount of urease is placed on the diffusion element and acts as a positive control for the test kit.

* * * * *